(12) United States Patent
Kunath et al.

(10) Patent No.: US 7,321,143 B2
(45) Date of Patent: Jan. 22, 2008

(54) ION-SENSITIVE FIELD EFFECT TRANSISTOR AND METHOD FOR PRODUCING AN ION-SENSITIVE FIELD EFFECT TRANSISTOR

(75) Inventors: Christian Kunath, Dresden (DE); Eberhard Kurth, Moritzburg (DE)

(73) Assignee: Fraunhofer-Gesellschaft zur Forderun der Angewandten Forschung E.V., Munich (DE)

(*) Notice: Subject to any disclaimer, the term of this patent is extended or adjusted under 35 U.S.C. 154(b) by 135 days.

(21) Appl. No.: 11/210,420

(22) Filed: Aug. 24, 2005

(65) Prior Publication Data

US 2006/0035420 A1 Feb. 16, 2006

Related U.S. Application Data

(63) Continuation of application No. PCT/EP03/02359, filed on Mar. 7, 2003.

(51) Int. Cl.
*H01L 29/76* (2006.01)
(52) U.S. Cl. .................................. 257/288; 257/350
(58) Field of Classification Search ................ 257/288, 257/341, 350, 390
See application file for complete search history.

(56) References Cited

U.S. PATENT DOCUMENTS

| | | | |
|---|---|---|---|
| 5,288,563 A * | 2/1994 | Saito et al. ................ | 429/91 |
| 5,465,249 A * | 11/1995 | Cooper et al. ............. | 365/149 |
| 6,225,168 B1 * | 5/2001 | Gardner et al. ............ | 438/287 |
| 6,483,151 B2 * | 11/2002 | Wakabayashi et al. ...... | 257/369 |
| 6,560,142 B1 * | 5/2003 | Ando ........................ | 365/177 |
| 6,682,973 B1 * | 1/2004 | Paton et al. ................ | 438/240 |
| 2001/0025971 A1 * | 10/2001 | Powell ...................... | 257/288 |
| 2002/0008261 A1 * | 1/2002 | Nishiyama ................. | 257/288 |
| 2002/0022357 A1 * | 2/2002 | Iijima et al. ............... | 438/622 |
| 2002/0149065 A1 * | 10/2002 | Koyama et al. ........... | 257/389 |
| 2003/0064567 A1 * | 4/2003 | Chaudhry et al. ......... | 438/400 |
| 2003/0107073 A1 * | 6/2003 | Iijima et al. ............... | 257/296 |
| 2003/0211718 A1 * | 11/2003 | Koyama et al. ........... | 438/591 |
| 2004/0120092 A1 * | 6/2004 | Jaussi et al. ............... | 361/118 |
| 2004/0235285 A1 * | 11/2004 | Kang et al. ................ | 438/597 |

(Continued)

FOREIGN PATENT DOCUMENTS

EP  PCT/EP2003/002359    3/2003

(Continued)

OTHER PUBLICATIONS

S. Wakida, S. Mochizuki, R. Makabe, A. Kawahara, M. Yamane, S. Takasuka, K. Higashi; "PH-Sensitive ISFETS Based on Titanium Nitride and Their Application to Battery Monitor;" Material Chemistry Department, Material Physics Department, Government Idustrial Research Institute, Osaka, Japan; pp. 222-224, date unknown.

(Continued)

*Primary Examiner*—Thao P. Le
(74) *Attorney, Agent, or Firm*—Thomas, Kayden, Horstemeyer & Risley

(57) ABSTRACT

An ion-sensitive field effect transistor includes a substrate on which there are formed a source region and a drain region. Above a channel region, the ion-sensitive field effect transistor has a gate with a sensitive layer including a metal oxide nitride mixture and/or a metal oxide nitride mixture compound.

14 Claims, 1 Drawing Sheet

U.S. PATENT DOCUMENTS

2005/0218462 A1* 10/2005 Ahn et al. .................. 257/410
2006/0051925 A1* 3/2006 Ahn et al. .................. 438/287
2007/0063295 A1* 3/2007 Jeon et al. .................. 257/410

FOREIGN PATENT DOCUMENTS

| WO | WO 94/22006 | 9/1994 |
|---|---|---|
| WO | WO 2004/079355 | 9/2004 |

OTHER PUBLICATIONS

I. Gracia, C. Cane, M. Lozano, J. Esteve; "Test Structures for ISFET Chemical Sensors;" Proc. IEEE 1992 Int. Conference on Microelectronic Test Structures, vol. 5, Mar. 1992; pp. 156-159.

Database WPI; Section CH, Week 198521; Derwent Publications Ltd., London, GB, date unknown.

International Preliminary Examination Report, date unknown.

* cited by examiner

ION-SENSITIVE FIELD EFFECT TRANSISTOR AND METHOD FOR PRODUCING AN ION-SENSITIVE FIELD EFFECT TRANSISTOR

CROSS-REFERENCE TO RELATED APPLICATION

This application is a continuation of copending International Application No. PCT/EP03/02359, filed on Mar. 7, 2003, which designated the United States and was not published in English.

BACKGROUND OF THE INVENTION

1. Field of the Invention

The present invention relates to field effect transistors and particularly to ion-sensitive field effect transistors and a method for producing them.

2. Description of the Related Art

Ion-sensitive field effect transistors (ISFET) serve for measuring ionic concentrations or special substance concentrations in solutions of various compositions and conductivities. Applications of ion-sensitive field effect transistors are, for example, for the continuous detection of concentrations in environment monitoring, in industrial process monitoring, in the food industry, in biochemistry and medical technology, and in laboratory analytics. Here, in particular, a highly precise concentration detection and a minimal long-term drift of the sensor are required, which should further be combined with an acceptable price of the sensor.

It is known that ionic concentrations in aqueous media are measured with glass electrodes both in process measurement technology and in laboratory measurement technology. For technical reasons, particularly because a sufficiently large internal buffer volume combined with an also sufficiently coated internal bleeder electrode and an allowably stable glass membrane as sensor-active component are required, there is no possibility of an efficient miniaturization of the glass electrodes. The internal buffer volume and the coating of the internal bleeder electrode have to satisfy the requirements of the temperature-time load estimated for the sensor. On the other hand, due to the necessary glass membrane thickness, the pH measuring system of the glass electrode measuring chain is a high impedance system, which makes it susceptible to environmental disturbances. Among other things, this requires shielding of the measuring lines, wherein the distances between the electrodes, i.e. from the glass electrode to the reference electrode, and from the electrodes to the measuring device are to be minimized.

Another disadvantage of the glass electrodes is that there is the danger of them releasing sharp-edged glass splinters when breaking, so that the employment of glass electrodes is limited in certain areas, such as in the food industry.

In contrast to the glass electrodes, the usage of ion-sensitive field effect transistors represents a break-proof alternative to conventional glass electrodes. Furthermore, these sensors are suitable for the miniaturization of the measuring system, the production of integrated systems, and low-cost manufacturing, so that the ion-sensitive field effect transistor is superior to the conventional glass electrode with respect to the above aspects.

The application of ion-sensitive field effect transistors for the ionic concentration measurement and particularly for the measurement of the pH value in aqueous media has been known for a long time, and is described, for example, in the document Bergveld P., IEEE Trans. Biomed. E 17 (1970) 70.

For producing hydrogen ion-sensitive layers of the ion-sensitive field effect transistors, various materials, such as $SiO_2$, $Si_3N_4$, $Al_2O_3$, $Al_xSi_yO_z$, $ZrO_2$, $Ta_2O_5$ and diamond-like carbon (DLC) have already been examined and described. In this respect, see the documents Van der Schoot et al., Sensors & Actuators 4 (1983), 267; Sobczynska D. et al., Sensors & Actuators 6 (1984), 93; Klein M. et al., VDI-Berichte 509 (1983), 275; Sakai T. et al., Internat. Electron Devices Meeting, Techn. Digest (1987), 711; Abe H. et al., IEEE Trans. Electron. Dev. ED-26 (1979), 1939. The introduction of the metal oxide layers achieved significant improvements of the sensor properties as compared to the ion-sensitive field effect transistors with a sensitive layer of $Si_3N_4$, particularly with respect to pH sensitivity, pH sensor linearity, pH selectivity, i.e. cross-sensitivity to other than the $H^+$ ion to be measured, hysteresis behavior, response behavior, start-up time, photosensitivity, drift and long-term stability. The most advantageous sensor properties of ion-sensitive field effect transistors are known to have been achieved with a sensitive layer of $Ta_2O_5$.

However, the usage of metal oxides as sensitive layer has the disadvantage that, due to the crystalline structure of the metal oxides after the necessary annealing processes, the settling times of these sensors when changing the measured solution is larger than with the ion-sensitive field effect transistors with the normally amorphous $Si_3N_4$ layers.

Without sufficient annealing processes, the metal oxide layers do not achieve the advantages over the sensitive layers of $Si_3N_4$. A further improvement in the sensor stability of ion-sensitive field effect transistors in aggressive media, such as bases and hydrofluoric acids, is ascribed to the carbon-based layers, wherein, however, their response behavior is less favorable than with a sensitive layer of $Si_3N_4$.

The areas of application of the above ion-sensitive field effect transistors with metal oxide layers are mostly restricted to limited pH ranges and temperature ranges of the solutions. Therefore, there has been no consistent introduction of pH measurements on the basis of ion-sensitive field effect transistors in the industrial process measurement technology or in environment monitoring yet, so that there has been no addition to or substitution of the glass electrodes in these areas.

It is particularly to be mentioned in this respect that all above layer materials are single component systems, i.e. they are simple, pure compounds limited in acidity with respect to their single pH sensitive component, e.g. [TaOH] in the case of $Ta_2O_5$, after the hydrolysis of the surface in the solution. This means that the single component systems become non-linear in basic or acid solutions, because there is only one defined $pK_s$ and one $pH_{PZC}$. The limited acidity is further the reason for irreversible damages in the sensor layer at high temperatures. In the case of the glass electrode, the sensor-active layer is an $SiO_2$-based glass with a slight addition of various metal oxides, which both linearize the acidity of the [SiOH] better and increase the stability with respect to bases and acids than would be the case with a pure semi-metal oxide $SiO_2$.

The necessity of a glass structure of the sensitive layer does not exist for the ion-sensitive field effect transistor. That is why the properties of the glass structural substance $SiO_2$ that are disadvantageous with respect to the sensor can be avoided in the same. Such disadvantageous properties are the changing sensor properties by solutions containing hydrofluoric acid and the cross-sensitivity to alkali ions, particularly $Na^+$ ions (see, for example, Bergveld P., IEEE Trans. Biomed. E 17 (1970), 70). Then, a lower pH value is indicated in basic solutions with Na$^+$ ions than would correspond to the real H$^+$ ion concentration. Particularly at elevated temperatures, the pH sensor properties irreversibly deteriorate more and more in these basic solutions and finally the lifetime is limited, because SiO$_2$ is dissolved in strong alkaline solutions. The lifetime is further limited by the etching in solutions containing hydrofluoric acid. In practice, the metal oxide additions are changed to either increase the stability in aggressive media or to reduce cross-sensitivity, wherein, however, the structural substance SiO$_2$ limits the adjustment possibilities, so that only a limited improvement of the electrode is possible.

Furthermore, cross-sensitivities to alkali ions may also occur at surfaces of metal silicates, which may be more pronounced in the case of aluminosilicates Al$_x$Si$_y$O$_z$ than in purely thermal SiO$_2$ (see, for example, Abe H. et al., IEEE Trans. Electron. Dev. ED-26 (1979), 1939, or Esashi M., Matsuo T., IEEE Trans. Biomed. BME-25 (1978), 184). It is further known, see, for example, Leistiko O., Physica Scripta 18 (1978), 445, that pure thermal SiO$_2$ has a lower cross-sensitivity to Na$^+$ and K$^+$ ions in ion-sensitive field effect transistors, wherein, however, there is a strong hysteresis of ±0.2 pH and a considerably lower transconductance of about 30 mV/pH as compared to a glass electrode with >58 mV/pH. The document Bergveld P., IEEE Trans. Biomed. E 17 (1970) 70, observed an increased cross-sensitivity to Na$^+$ ions, which was due to an Al gate on the SiO$_2$ having been etched away after the CMOS process. Even minor temperings at about 400° C. in forming gas annealing are sufficient to form monolayers of aluminosilicate on the SiO$_2$, which considerably change the pH sensor properties. By forming the aluminosilicate, the chemical stability could be increased, which, however, resulted in a decrease of the pH sensitivity.

Another disadvantage of pure metal oxide compounds is that their molecular structure is only adjustable to a limited extent by temperature-time processes. High temperatures after the layer deposition result in the necessary consolidation and freedom of structural defects of the metal oxide and thus in a good chemical stability of the layer, but also in crystallization and thus formation of pronounced disturbances of the surface which may reach all the way to the substrate. However, it is required for a good property of the sensor that the sensor surface is homogeneous, smooth and closed.

SUMMARY OF THE INVENTION

It is the object of the present invention to provide an ion-sensitive field effect transistor with improved sensor properties.

In accordance with a first aspect, the present invention provides an ion-sensitive field effect transistor with a gate having a sensitive layer, wherein the sensitive layer has a metal oxide nitride mixture and/or a metal oxide nitride mixture compound.

In accordance with a second aspect, the present invention provides a method for producing an ion-sensitive field effect transistor, having the steps of providing a substrate with a source region and a drain region; and providing a gate with a sensitive layer, wherein the sensitive layer includes a metal oxide nitride mixture and/or a metal oxide nitride mixture compound.

The present invention provides an ion-sensitive field effect transistor with a gate having a gate with a sensitive layer of a metal oxide nitride mixture and/or a metal oxide nitride mixture compound.

The present invention further provides a method for producing an ion-sensitive field effect transistor, having the following steps:

providing a substrate with a source region and a drain region; and generating a gate with a sensitive layer having a metal oxide nitride mixture and/or a metal oxide nitride mixture compound.

The present invention is based on the finding that an ion-sensitive field effect transistor with improved sensor properties may be achieved by the gate having a sensitive layer of a metal oxide nitride mixture and/or a metal oxide nitride mixture compound. A metal oxide nitride mixture is considered to be any composition resulting from a first metal M1, a second metal M2, oxygen O and nitrogen N. A metal oxide nitride mixture compound is considered to be any compound resulting from a metal oxide nitride mixture with another chemical element or another chemical compound. For example, metal oxide nitride mixtures and metal oxide nitride mixture compounds belong to the class of the oxynitrides, among others the system Hf$_a$Ta$_b$O$_c$N$_d$, characterized by a high chemical stability.

Mixing two or more metal oxides results in several pK$_s$ (pK$_s$=negative logarithm of the dissociation constant), whereby the linear pH range of the sensor is extended and a non-linear range is reduced or eliminated, wherein further the cross-sensitivity is reduced and a high chemical stability is achieved. In the class of the oxynitrides, for example, several pK$_s$ and/or the magnitude of individual pK$_s$ may be adjusted by an exact composition, for example a, b, c and d, of Hf$_a$Ta$_b$O$_c$N$_d$, so that the condition for a more extensive pH linearity is met.

Furthermore, the lifetime of the ion-sensitive field effect transistor is increased by the possibility to produce acid/base-complementary mixtures and/or compounds, because, for example in the case of excessive stresses by strong acids at high temperatures or by strong bases at high temperatures, a partial component as passive monolayer always stops the dissolution of the sensor layer. Thereby, a silicate component can be dispensed with, which might possibly increase the cross-ion sensitivity to alkali ions, without a decrease in the stability with respect to hydrofluoric acid.

The inventive sensitive layer may consist of only one material or may also comprise several layers of different materials disposed one on top of the other. In one embodiment, the sensitive layer may also include several layers having different concentrations of the elements disposed one on top of the other.

The use of defined additions of further metal oxides and nitrogen further increases the stability of amorphous and nanocrystalline structures at elevated annealing temperatures, thus avoiding grain boundaries. Mixing two or more metal oxides allows an increased consolidation of the material by the different metal atom diameters without the occurrence of crystallization, or a minimization of the crystallinity or grain boundary intensity and a maximization of the amorphous character by the addition of nitrogen at a maximum annealing temperature and annealing time. This allows to avoid the crystalline modifications occurring in prior art during temperature treatments of simple metal oxides for the improvement of the chemical stability, which have a negative effect in prior art, because they result in weak points at the grain boundaries which favour ion diffusion, increase drift or affect photosensitivity.

According to an embodiment, the amorphous and/or nanocrystalline structure advantageous for the sensor properties may be guaranteed by variation of the nitrogen content in the layer.

Furthermore, the expansion coefficient of the sensitive layer may be adjusted by mixing two or more metal oxides by specific stoichiometric ratios of various metal oxides. The adaptation of the expansion coefficient may be performed with respect to the gate oxide, preferably including $SiO_2$, or the substrate, preferably including Si. Furthermore, between the sensitive layer of a metal oxide nitride mixture or a metal oxide nitride mixture compound and the gate oxide, there may be provided one or more interface layers which may include metal oxide silicates and/or metal oxide nitride silicates. As a consequence of the adaptation of the expansion coefficients, the layers do not tear by the heating and cooling procedures of the annealing tempering and a minimization of the tensile and compressive stresses of the layers at all process temperatures is achieved.

The sensitive layer may be deposited directly or onto an $SiO_2$ layer serving as transition layer or as adhesive layer.

Furthermore, the inventive ion-sensitive field effect transistor has improved properties of the transistor parameters. It is known that, besides the sensor properties, the reproducibility of the transistor parameters is also decisive for the application of ISFET sensors.

The transistor parameters determine the working point position of the sensor and the spread of the sensor parameters. The basis of homogeneous transistor parameters is the control of the isolator interfaces to the silicon and, in the case of multiple layers, between the layers. Due to the specific adjustment of defined compounds, such as $Hf_aTa_b\text{-}O_cN_d$, with monocrystalline or amorphous structure and homogeneous interface transitions all the way to the substrate, transistors may be produced that meet these conditions. This is achieved by the fact that isolator layers may be constructed by a free adjustment of the parameters a, b, c, and d, which have a homogeneous transition from the substrate to the sensitive surface. Furthermore, the crystallization behavior during temperature treatment can be determined by the ratio of oxygen to nitrogen in the compound. Thus, due to the variability of the element ratios, sensors with a high chemical stability combined with a quick response may be produced.

The use of metal oxide nitride mixtures and metal oxide nitride mixture compounds as sensitive layer of an ion-sensitive field effect transistor therefore allows a pH measurement precision as compared to the known ion-sensitive field effect transistors which had not been reached up to now, without the large effort of a $Pt\text{-}H_2$ electrode, combined with an even higher chemical stability as compared to the simple metal oxide compounds and/or metal nitride compounds, such as $HfO_2$ and $Ta_2O_5$.

In one embodiment, for example, the sensitive layer may comprise a concentration gradient of one of the elements of the metal oxide nitride mixture and/or the metal oxide nitride mixture compound, i.e. for example a gradient of the concentration of one of the metals, a gradient of the oxygen or a gradient of the nitrogen. This may achieve that the direct surface area of the sensitive layer in contact with the measured liquid comprises an elevated chemical stability as compared to other areas of the sensitive layer to alleviate a destruction of the sensitive layer by aggressive measured media.

In one embodiment, the production of the inventive sensitive layer of a metal oxide nitride mixture and/or metal oxide nitride mixture compound may be performed in a simple manner by overcoating a first metal oxide layer with a second layer of another metal, a metal alloy or a metal oxide and by generating a mixture on the surface of the first metal oxide layer by appropriate temperings and temper gases. Subsequently, the areas of the second layer which were not chemically altered by the tempering are removed by etching.

The production method described above further has the advantage that, by the overcoating with a metal or a metal alloy, the sensitive channel area is protected for a certain time from environmental disturbances, particularly from electric fields. By the metallic protection over the channel, the transistor parameters become more reproducible. Furthermore, the overcoating helps to improve an already existing insufficient consolidation of the first metal oxide, whereby good structural properties of the sensitive layer may be achieved in a simple manner by the production method.

Due to the good sensor properties and a high reproducibility of the transistor parameters, the ion-sensitive field effect transistor on the basis of metal oxide nitride mixtures or metal oxide nitride mixture compounds is suitable for a highly stable sensor for the use in industrial process measurement technology and environment monitoring. Due to the amorphous and/or monocrystalline layer design and the related high settling speed, this sensor further has a large potential of usage in medical technology. Particularly favorable properties may be achieved by using hafnium tantalum oxide nitride mixtures and hafnium tantalum oxide nitride mixture compounds and by zirconium tantalum oxide nitride mixtures and zirconium tantalum oxide nitride mixture compounds.

BRIEF DESCRIPTION OF THE DRAWINGS

Preferred embodiments of the present invention are explained below in more detail with respect to the accompanying drawings, in which.

DESCRIPTION OF THE PREFERRED EMBODIMENTS

Figure 1:
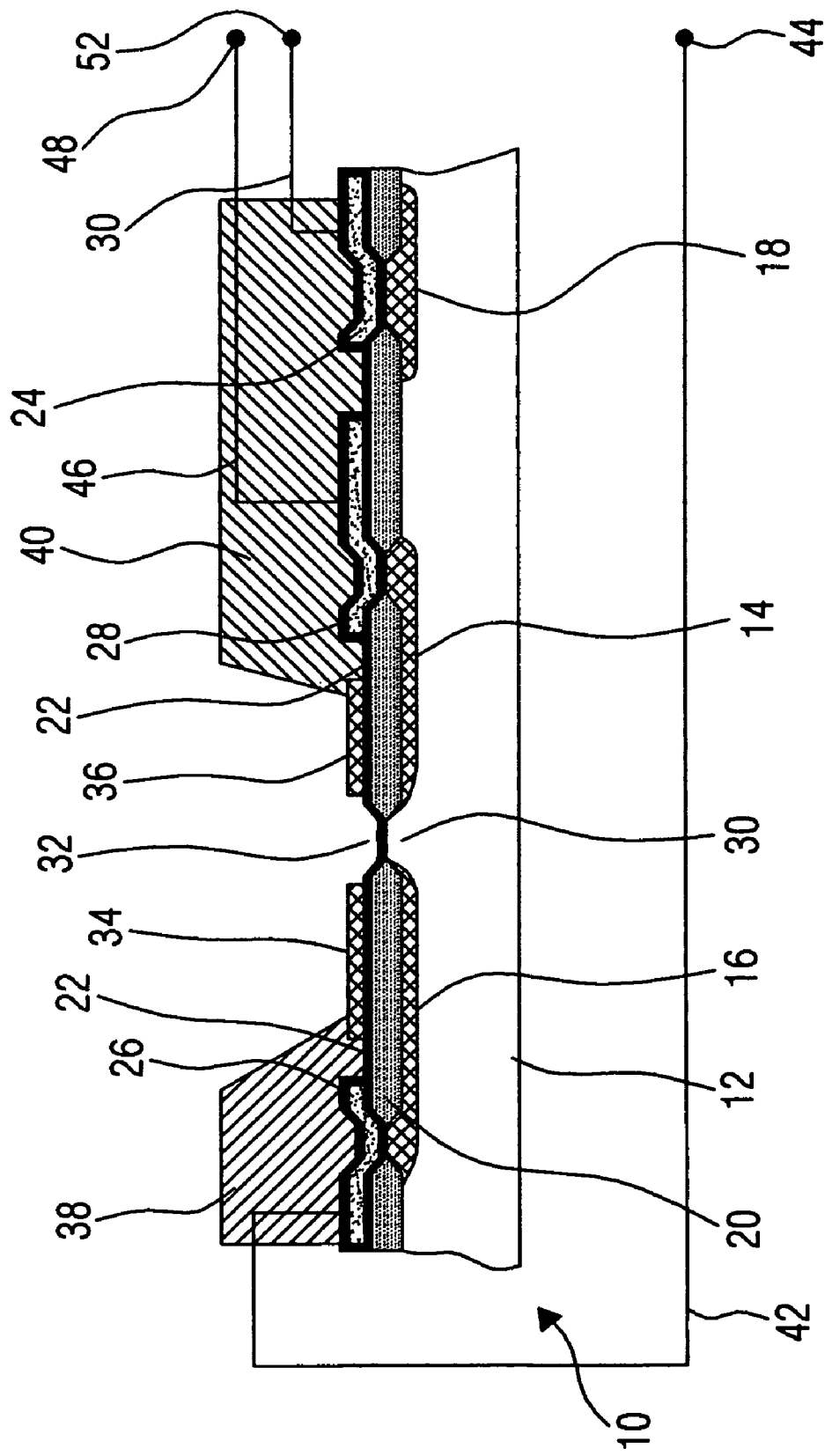
FIG. 1 shows a cross-sectional illustration of an ion-sensitive field effect transistor according to a preferred embodiment of the present invention.

FIG. 1 shows a cross-sectional illustration of an ion-sensitive field effect transistor (ISFET) 10. The ion-sensitive field effect transistor 10 includes a semiconductor substrate 12, e.g. a silicon substrate. In the substrate 12, there are formed a source region 14 and a drain region 16. The substrate further comprises a substrate terminal region 18. The substrate may be a combination of a carrier substrate and an epitaxy layer deposited thereon, in which there are formed the active regions of the device. A field oxide layer 20 is formed on a surface of the substrate 12. A further isolating layer 22 extends on the field oxide layer 20.

The field effect transistor 10 further includes a terminal contact 24 which extends through the field oxide layer 20 and the isolating layer 22 and is connected to the substrate terminal region 18. Further, the field effect transistor 10 includes a drain contact 26 that extends through the field oxide layer 20 and the isolating layer 22 and is connected to the drain region 16. Further, a source contact 28 is formed that extends through the field oxide layer 20 and the isolating layer 22 and is connected to the source region 14.

A channel region 30 is defined between the source region 14 and the drain region 16. Above the channel region 30, there is formed a gate 32 which, according to the invention, comprises a sensitive layer of a metal oxide nitride mixture or a metal oxide nitride mixture compound which gets into direct contact with the measured medium during a measurement. As shown in FIG. 1, the sensitive layer 32 may be formed contiguous with the isolating layer 22. In one embodiment, the isolating layer 22 may consists of the material of the sensitive layer 32, i.e. of a metal oxide nitride mixture or a metal oxide nitride mixture compound.

According to FIG. 1, the field effect transistor 10 includes further isolation layers 34 and 36 which are formed, respectively, lateral to the channel region 30 on the isolating layer 22. On the drain contact 26, there is further formed a first passivation layer 38. The field effect transistor 10 further comprises a second passivation layer 40 extending across the source contact 28 and the substrate terminal contact 24. The drain contact 26 is connected to a drain terminal 44 via a line 42, the source contact 28 is connected to a source terminal 48 via a line 46, and the substrate terminal 24 is connected to a substrate terminal 52 via a line 50.

The production of the inventive ion-sensitive field effect transistor may preferably be performed in a CMOS process. This allows a low-cost production and an integration of further circuit members on the substrate 10.

The sensitive layer 32 is preferable produced by sputtering the metal or the metal oxide in an oxygen-$N_2$ atmosphere or by CVD deposition. For annealing and improving the layer properties, a temperature treatment may subsequently be performed at temperatures of >500° C. in an atmosphere with inert or oxidizing or nitridizing properties or their desired properties.

The ion-sensitive field effect transistor is preferably disposed on a chip with an area of about 3.5×3.5 mm$^2$ and is produced in a group on 150 mm silicon wafers in a semiconductor line. After dicing the wafer into chips, the diced chips are glued to suitable substrates, contacted and completed by means of special construction methods to complete measuring systems. Immersion electrodes for pH measurement are, for example, produced from the chips and/or boards.

One embodiment provides to deposit the sensitive layer 32 directly onto the substrate, i.e. onto the channel region of the substrate 10. Here the sensitive layer 32 acts both as gate isolation layer and as sensitive layer allowing the ion-sensitive detecting.

Furthermore, the inventive sensitive layer of a metal oxide nitride mixture or a metal oxide nitride mixture compound may be generated by sputtering a metal which, in a subsequent step, is oxidized and nitridized.

The inventive use of the metal oxide nitride mixture or compounds of the same further allows, by means of adjustments of parameters during the production method, that the sensitive layer comprises a structure between amorphous and nanocrystalline. This may be achieved, for example, by suitably adjusting the deposition and the post-treatment.

For adapting the expansion coefficient, interface layers may be formed on surfaces of the sensitive layer. The interface layers include, for example, metal oxide silicates and/or metal oxide nitride silicates which are deposited by tempering or by sputtering and/or CVD depositing (CVD=chemical vapour deposition).

During operation of the ion-sensitive field effect transistor as measuring sensor for the detection of, for example, ionic concentrations of a measured fluid, the ion-sensitive field effect transistor is put into contact with the measured medium such that a surface of the sensitive layer 32 has contact with the measured medium. Furthermore, a reference electrode, which may, for example, consist of Ag, AgCl and KCl, is introduced into the measured medium.

A drain-source current is effected via a voltage source applying an electrical voltage between the drain terminal and the source terminal, wherein the substrate terminal contact is put to a reference potential, e.g. ground.

Due to a different electrochemical voltage valence of the materials of the reference electrode and the sensitive layer of the gate, an electrical voltage forms between the reference electrode and the gate, depending on an ionic concentration of the measured medium. In a preferred embodiment, the voltage source controls the drain-source voltage so that there always flows a constant drain-source current. In this embodiment, the electrical voltage between the reference electrode and the gate changes depending on the ionic concentration of the measured medium, wherein the voltage applied between the source and the reference electrode represents a measured quantity depending on an ionic concentration of the measured medium.

In one embodiment, the inventive ion-sensitive field effect transistor may comprise a p-doped substrate, wherein the source regions and the drain regions are formed as n-doped regions. Further, the ion-sensitive field effect transistor may include an n-doped substrate with p-doped source and drain regions.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. An ion-sensitive field effect transistor with a gate comprising a sensitive layer, wherein the sensitive layer comprises a metal oxide nitride alloy and/or a metal oxide nitride compound, wherein the metal oxide nitride alloy is a hafnium tantalum oxide nitride alloy and the metal oxide nitride compound is a hafnium tantalum oxide nitride compound.

2. An ion-sensitive field effect transistor with a gate comprising a sensitive layer, wherein the sensitive layer comprises a metal oxide nitride alloy and/or a metal oxide nitride compound, wherein the metal oxide nitride alloy is a zirconium tantalum oxide nitride alloy and the metal oxide nitride compound is a zirconium tantalum oxide nitride compound.

3. The ion-sensitive field effect transistor of claim 1, wherein the sensitive layer is deposited directly on a channel region of a substrate or directly on a gate isolation layer.

4. The ion-sensitive field effect transistor of claim 1, wherein, for compensating different expansion coefficients, one or more adaptation layers are deposited between the substrate and the sensitive layer, which preferably include metal oxide silicates and/or metal oxide nitride silicates.

5. A method for producing an ion-sensitive field effect transistor, comprising:
providing a substrate with a source region and a drain region; and
providing a gate with a sensitive layer, wherein the sensitive layer includes a metal oxide nitride alloy and/or a metal oxide nitride compound, wherein the metal oxide nitride alloy is a hafnium tantalum oxide nitride alloy and the metal oxide nitride compound is a hafnium tantalum oxide nitride compound.

6. The method of claim 5, wherein the sensitive layer is generated by sputtering or by chemical gas phase deposition.

7. The method of claim 5, further comprising the step of tempering the sensitive layer for adjusting sensor properties.

8. The method of claim 5, wherein generating the sensitive layer includes adjusting parameters in depositing and/or post-treating the sensitive layer such that its structure is between amorphous and nanocrystalline.

9. The method of claim 5, further comprising the step of generating interface layers between the substrate and the sensitive layer for adapting their respective expansion coefficients.

10. The method of claim 9, wherein the interface layers include metal oxide silicates and/or metal oxide nitride silicates.

11. The method of claim 10, wherein generating interface layers is performed by means of tempering, sputtering or chemical gas phase deposition.

12. The ion-sensitive field effect transistor of claim 2, wherein the sensitive layer is deposited directly on a channel region of a substrate or directly on a gate isolation layer.

13. The ion-sensitive field effect transistor of claim 2, wherein, for compensating different expansion coefficients, one or more adaptation layers are deposited between the substrate and the sensitive layer, which preferably include metal oxide silicates and/or metal oxide nitride silicates.

14. A method for producing an ion-sensitive field effect transistor, comprising:

providing a substrate with a source region and a drain region; and providing a gate with a sensitive layer, wherein the sensitive layer includes a metal oxide nitride alloy and/or a metal oxide nitride compound, wherein the metal oxide nitride alloy is a zirconium tantalum oxide nitride alloy and the metal oxide nitride compound is a zirconium tantalum oxide nitride compound.

* * * * *